US008601731B2

(12) United States Patent
Padgett et al.

(10) Patent No.: US 8,601,731 B2
(45) Date of Patent: Dec. 10, 2013

(54) TWO-PIECE WRISTBAND WITH INTERCHANGEABLE LASSO BAND ELEMENT FOR USER SELECTABLE SIZING

(71) Applicant: Disney Enterprises, Inc., Burbank, CA (US)

(72) Inventors: John M. Padgett, Clermont, FL (US); Michael G. Jungen, Orlando, FL (US); John David Worrall, Clermont, FL (US); Maxmillian Philip Burton, San Francisco, CA (US); Carson Lau, San Francisco, CA (US); Adam D. Leonards, El Cerrito, CA (US)

(73) Assignee: Disney Enterprises, Inc., Burbank, CA (US)

( * ) Notice: Subject to any disclaimer, the term of this patent is extended or adjusted under 35 U.S.C. 154(b) by 0 days.

(21) Appl. No.: 13/867,889

(22) Filed: Apr. 22, 2013

(65) Prior Publication Data

US 2013/0227988 A1 Sep. 5, 2013

Related U.S. Application Data

(63) Continuation of application No. 13/477,841, filed on May 22, 2012, now Pat. No. 8,479,426, which is a continuation of application No. 12/714,778, filed on Mar. 1, 2010, now Pat. No. 8,205,370.

(51) Int. Cl.
*A44C 5/00* (2006.01)

(52) U.S. Cl.
USPC .......................................................... 40/633

(58) Field of Classification Search
USPC .......... 40/633, 665, 304; 63/3.1, 3.2; 224/175
See application file for complete search history.

(56) References Cited

U.S. PATENT DOCUMENTS

| 4,742,503 | A | | 5/1988 | Braun et al. |
| 4,906,025 | A | | 3/1990 | Schreindl |
| 5,065,376 | A | | 11/1991 | Choulat |
| 5,235,567 | A | * | 8/1993 | Goodwin ...................... 368/282 |
| 5,416,953 | A | | 5/1995 | Hui |
| 7,041,032 | B1 | | 5/2006 | Calvano |
| 7,348,888 | B2 | | 3/2008 | Girvin |
| 7,481,370 | B2 | | 1/2009 | Davis |

(Continued)

OTHER PUBLICATIONS

Wristloks, http://www.adsources.com/CATALOG/wristlocks.htm, retrieved on Dec. 14, 2009, Wristlocks Wristbands.

(Continued)

*Primary Examiner* — Joanne Silbermann
(74) *Attorney, Agent, or Firm* — Marsh Fischmann & Breyfogle, LLP; Kent A. Lembke

(57) ABSTRACT

A wearable band with an adjustable size or length. The band includes a first band element with a raised center or identification member. The band includes a second band element with a body having a loop or lasso at one end defined by an inner surface of a sidewall. The outer sidewall of the raised center member is detachably coupled to the inner surface of the loop-defining sidewall when the center member is received within and captured by the loop such as by a snap detent arrangement. To allow sizing, the second band element includes both an inner band sizing element including the loop-defining sidewall at one of its ends and an outer band sizing element that is detachably coupled to the inner band sizing element. The length of the second band element is defined by the combined length of the inner and outer band sizing elements.

17 Claims, 12 Drawing Sheets

(56) References Cited

U.S. PATENT DOCUMENTS

| | | |
|---|---|---|
| 2005/0108912 A1 | 5/2005 | Bekker |
| 2005/0166436 A1* | 8/2005 | Girvin et al. .................... 40/633 |
| 2005/0262747 A1 | 12/2005 | Ali et al. |
| 2006/0144881 A1 | 7/2006 | Bonadei |
| 2009/0096614 A1 | 4/2009 | Singleton et al. |

OTHER PUBLICATIONS

Synometrix, http://www.synometrix.com/china_taiwan_rfid_bracelets.shtml, RFID Wristbands & RFID Bracelets & FRID Bracelet Manufacturers China Asia, retrieved on Dec. 14, 2009.

* cited by examiner

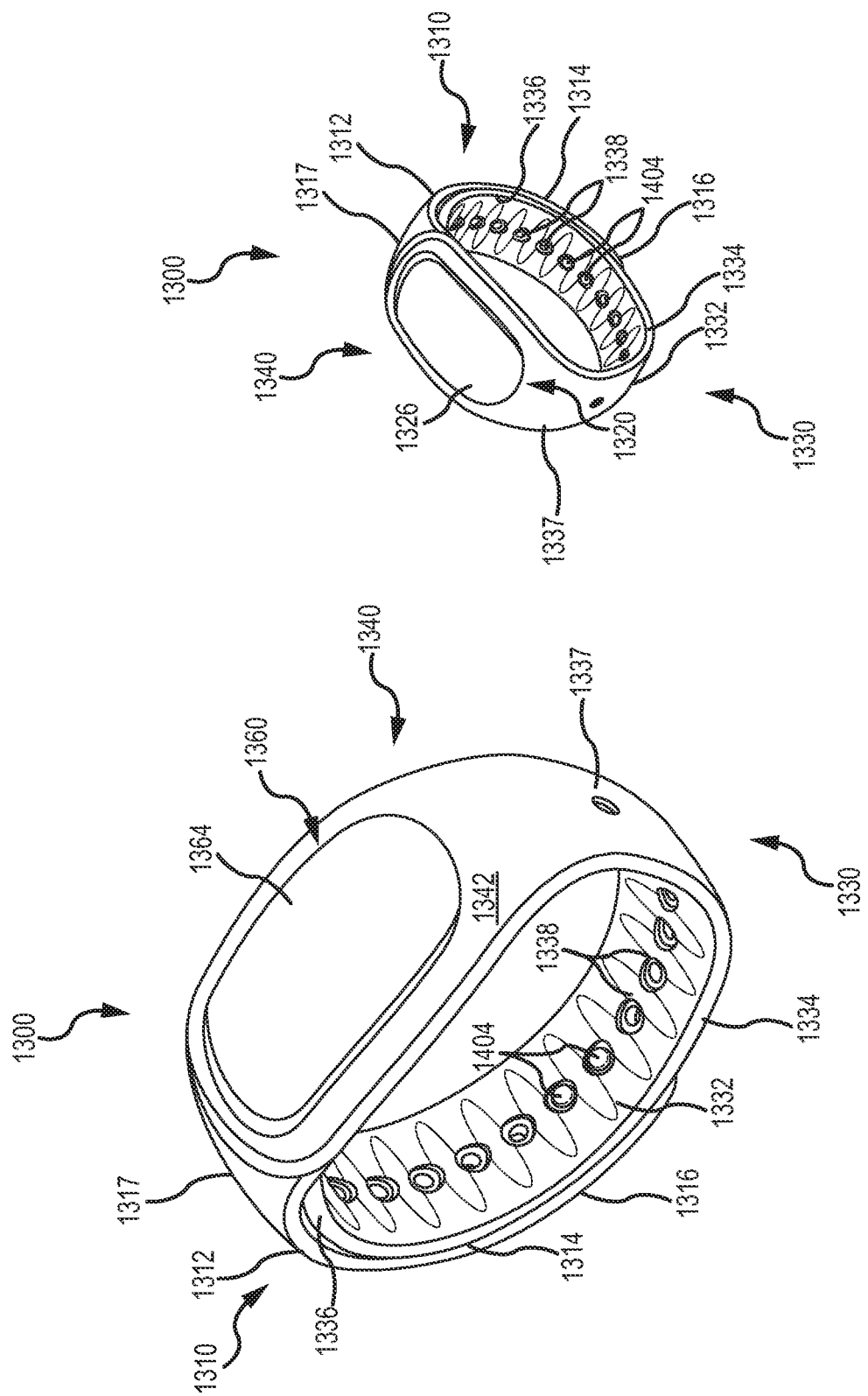

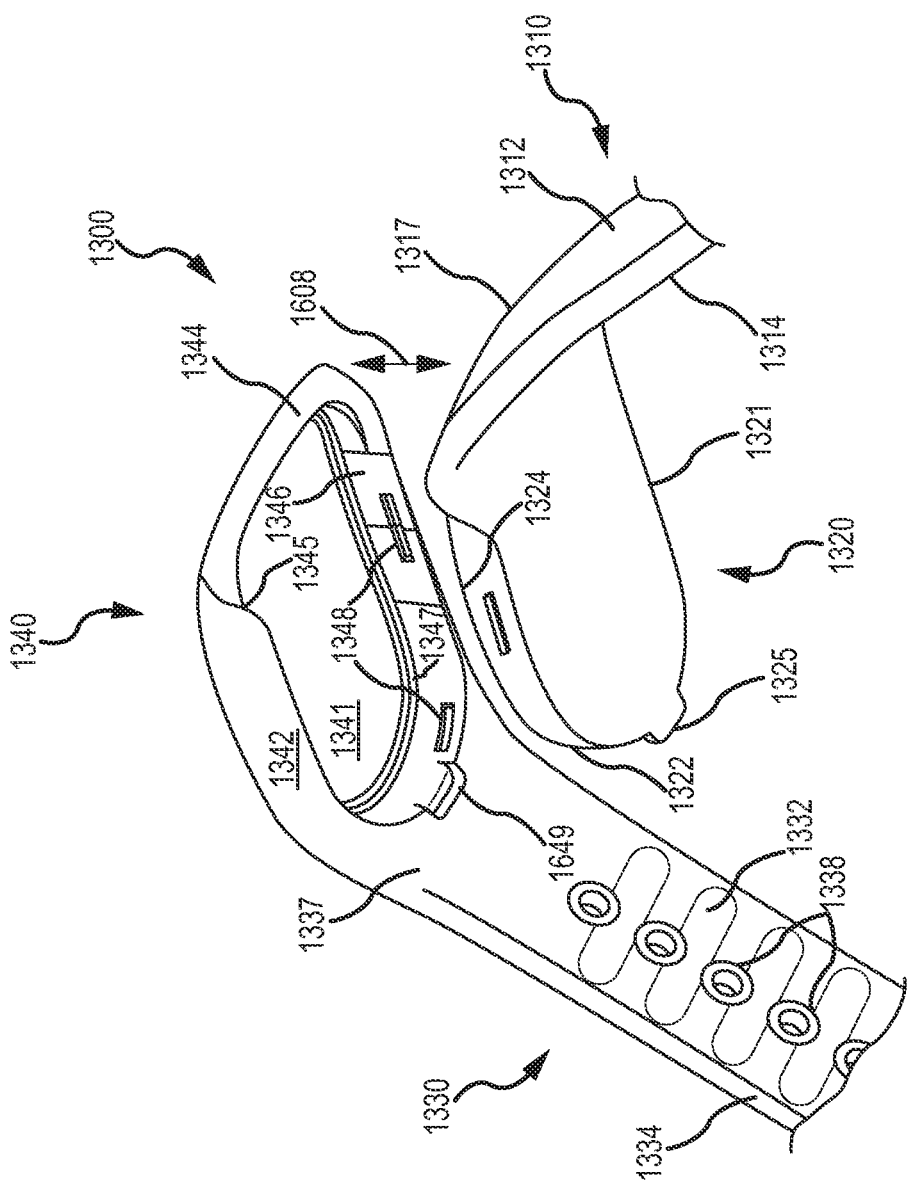

TWO-PIECE WRISTBAND WITH INTERCHANGEABLE LASSO BAND ELEMENT FOR USER SELECTABLE SIZING

CROSS-REFERENCE TO RELATED APPLICATIONS

This application is a continuation of U.S. patent application Ser. No. 13/477,841, filed on May 22, 2012, which is a continuation of U.S. patent application Ser. No. 12/714,778, filed on Mar. 1, 2010, now U.S. Pat. No. 8,205,370, both of which are hereby incorporated by reference in their entireties.

BACKGROUND

1. Field of the Description

The present description relates, in general, to wearable bands such as wristbands that are adjustable in size, and, more particularly, to wearable band assemblies that include a multi-sizing mechanism provided by a two-piece band design, e.g., including a lasso band element that mates with a base (or identification) band element, that allows the band to be sized in a tool-less manner by a user or wearer.

2. Relevant Background

Bands such as wristbands are worn in numerous settings. For example, watches have typically been worn on a wrist through the use of a wristband. In hospitals, patients often are provided an identification bracelet, strap, or band that they wear on their wrist. An amusement or theme park may provide a visitor or guest with a wristband that includes identification information or technology (e.g., a readable bar code, a radio frequency identification (RFID) transceiver or module, or the like) that identifies the visitor and allows the visitor to access the park's facilities. Often, bands are worn as fashion accessories or to allow the wearer to make a statement (e.g., to support a cause such as medical research, a political candidate, a sports team, or the like). It is likely that the demand for wearable bands such as wristbands will continue to grow in the coming years.

One ongoing challenge for the makers of wristbands and other wearable bands is providing proper sizing for the end users. For example, most multi-size wristwatches include a first band portion that is attached at a first end to the timepiece and at a second end may have a number of spaced apart holes. A second band portion is attached at its first end to the timepiece and at its second end may contain a buckle-style clasp mechanism for mating with the holes of the first band portion. A person uses the clasp mechanism to both size the band about their wrist and to also lock the timepiece to their wrist. The wristwatches are multi-size in that the spaced apart holes allow the same wristwatch to be worn by a set of people whose wrists have a size that falls within a predefined range (e.g., a minimum and maximum sized wrist diameter defined by the first and last hole on the band).

However, people outside this predefined range would not be able to wear the wristwatch, and the wristwatch manufacturer either simply loses these sales or may provide additional wristwatches that have different size ranges to suit these other buyers. Unfortunately, this requires added inventory that may or may not be sold. Some efforts have been made to provide band designs that allow the band to be sized for a particular person, but these designs typically require specialized tools to adjust the band and are expensive to manufacture. In other cases, a band selected for a user to match their wrist size may be attached to the timepiece, but, again, this typically requires a special tool for attachment of the band to the timepiece and may require the buyer to have the watch sized by a trained technician.

As another example of the use of wearable bands, RFID wristbands are commonly used in hospitals and entertainment venues to identify individual patients and guests. The wristband may include or provide a link to a variety of information such as the person's name, their room number, a seating location for a show, entitlements permitted in the hospital or venue, and so on. The wristband is often designed to be secured or locked onto the wrist of the person during their stay at the hospital or participation in an entertainment event.

While these wristbands have been useful in identifying the patients and guests, their design has typically not effectively accommodated the wide range of users' wrist sizes, which has resulted in many users having very loose or too tight and uncomfortable fitting wristbands. Additionally, many wristband designs use either an adhesive closure that is peeled away from the wristband or a separate, one-time plastic snap closure. The adhesive closures sometimes do not provide the closing strength desired and once removed, cannot be worn again. The plastic snap closures provide greater closing strength but often are intentionally designed for one time use, which limits use of these bands on an ongoing or repeated basis. Further, the snap closures often do not support a large enough range of wrist sizes such that they are often too tight or cannot be worn comfortably or are too loose which may allow them to fall off.

Accordingly, there remains a need for a low cost, multi-sizing mechanism for RFID wristbands and other wearable bands or straps. The band designs preferably would have durable opening and closing features to allow reuse of the band and would support relatively inexpensive manufacture from a variety of available materials such as plastics, silicones, metals, leathers, cloths, and/or other materials used presently (and in the future) for wearable bands. Further, there is a need for such a multi-sizing mechanism to be more fully adjustable to the wearer's wrist size, to provide a secure fastening mechanism that during regular wear can be fastened and unfastened by the wearer with ease, and to provide an aesthetic appearance that accommodates different wrist sizes within a large audience or wearer demographic.

SUMMARY

To address the above and other problems with wearable bands such as identification bands, a wearable band design is provided that allows a wearer to easily adjust the size of the band to suit the size of their wrist (or other body part such as the ankle or neck) through the use of a "lasso" band element or extending/sizing band element that is looped over and connected to the base or identification band element. The lasso band element may itself be a multi-part assembly that allows a user to select a size such as by removing a layer or extension to its body.

It was recognized that prior techniques of providing multi-size wristbands and similar products seemed to either require large inventories or provided a disposable wristband that provided no ongoing revenue source (or source of additional product sales). The wearable band assemblies described herein provide a product platform in that they typically include a base portion (e.g., a band element with an RFID or other information technology component) and an interchangeable extending or sizing portion (e.g., a lasso or sizing band element) that may be sized by the user and readily attached and detached from the base portion. In this manner, the wristband assembly permits interchangeability with a wide range of wearable styles of merchandise product offerings as the lasso or sizing band element may be sold or distributed separately from the base portion so as to allow a user/wearer to later purchase differing band elements to personalize or modify their wristband or wearable band assembly. The base or identification band element, though, may be provided in a single (or limited number) of designs to simplify its design and reduce cost of its manufacture and distribution (or inventory costs as only one to several choices may be provided).

In some cases, a band assembly is provided that allows an RFID or other identification module to be worn by end-users that may have a wrist size falling within a relatively large range (or within two, three, or more wrist size ranges). The band assembly may be considered a two-piece design in that it includes: (a) a base or ID band element with a body that includes a user identification member such as an RFID tag or module at one end; and (b) a sizing or extending band element with a body or spoke that includes a loop or lasso at one end to loop around and attach to the base or ID band element (e.g., over the end containing the user identification member). The two interlocking bands cover or are useful with a defined wristband size range.

The sizing band element (or product portion of the assembly) may have two (or more) layers or band members that when coupled together form a first or largest size of the sizing band element. In one case, the two layers or band members are interconnected or coupled via their sidewalls that provide a zipper and/or snap mechanism (e.g., similar to a food storage bag closure device). Depending upon the user's wrist size, they may peel away the outer layer(s) to reveal a sizing band element with a desired length or size to suit their needs (e.g., sized when combined with the base/ID band element to provide a properly sized wristband). In such a manner, the band assembly design allows for one side or half of the wristband to be used to contain or provide the RFID module or information storage unit and for the other side or half of the wristband to be fully interchangeable and sizable, which allows their use as product modules by the designer and/or distributor of the wristbands while the base or ID band element may be thought of as the product platform.

More particularly, a wearable band is provided with an adjustable size or length. The band includes a first band element (or base band) with a body extending from a first to a second end, which includes a raised center member such as may be used to contain a user ID member (e.g., an RFID tag/module). The body of the first band element may have an outer shape and length as defined by an outer sidewall, and the body may be relatively thin and planar. The wearable band assembly further includes a second band element with a body extending from a first to a second end. The second end of this body may include a loop or lasso that is defined by an inner surface of a sidewall (or loop structure sidewall). In use, the outer sidewall of the raised center member/user ID module may be detachably coupled to the inner surface of the loop-defining sidewall (or to the loop structure) when the center member is received within and captured by the loop.

To provide sizing, the second band element (or band sizing assembly) may include an inner band sizing element including the loop-defining sidewall at one of its ends. The second band element may further include an outer band sizing element that is detachably coupled to the inner band sizing element. The length of the second band element is then defined by the combined length of the inner and outer band sizing elements so as to cover two ranges of wearers' wrist sizes by including both elements or removing/decoupling the outer band sizing element from the inner band sizing element.

The inner band sizing element may have an elongated, planar body and the outer band sizing element may include a pair of arms that extend along and selective couple with the body of the inner band sizing element. The coupling mechanism used to couple these two sizing elements may be a tongue and groove arrangement.

Further, to couple the lasso or loop to the raised center member, the outer sidewall of the raised member may have a recessed surface or groove while the inner surface of the loop sidewall may include a corresponding or matched rib or raised surface. In this manner, the second band element may be coupled to the first band element when the raised center or ID member is received in or inserted into the loop such that the two sidewalls are in abutting contact with the rib received or snapped into the recessed groove. The loop sidewall may be formed of an elastic or deformable material such as plastic or rubber to allow it to more readily be stretched about the raised center member.

BRIEF DESCRIPTION OF THE DRAWINGS

FIG. 14 illustrates the wearable band assembly of FIG. 13 after assembly (e.g., as it may appear when worn on a user's wrist);

FIG. 15 illustrates the wearable band assembly of FIG. 13 after assembly similar to FIG. 14 but without use of the optional cap or insert;

FIG. 16 illustrates a partial exploded or disassembled view of the wearable band assembly of FIG. 15 providing additional details of the lasso band element (or extending/sizing band element) and the base or identification band element;

DETAILED DESCRIPTION OF THE PREFERRED EMBODIMENTS

The following description is generally directed toward a wearable band such as a wristband that may be readily configured to one of two or more sizes by adding or removing sizing layers or members (or simply "band extensions" or the like). The included figures illustrate several embodiments of such a wearable band, but, prior to describing these band embodiments, it may be useful to more generally describe exemplary wearable bands (which may also be called wristbands herein for simplicity of explanation without being limited to use on a wrist) and advantages of such bands when compared with existing bands or straps. Additionally, the following description highlights use of the bands as RFID wristbands, but it will be understood based on the description that the bands can readily be used with nearly any identification technology (such as barcodes or the like) as well as for bands without identification technologies/readable information. For example, the bands may be used with timepieces/watches or as products worn for fashion or other reasons.

Generally, the wearable bands described herein are designed to address or solve the multi-sizing and fastening mechanism problem that faces makers of wrist and other bands. The bands are easy for end users to assemble or configure into a particular size and allow interchanging of band layers/elements to personalize the bands. The bands are also adapted to make manufacture relatively inexpensive as its two-piece design provides a base band component or element (e.g., a band piece (or half of a wristband) that contains the identification module such as RFID tag or module) and a band sizing assembly. The base band element and the band sizing assembly are coupled together and function together to provide a multi-size band that can be used by all or a large portion of the population. The supply chain is also simplified in this manner as one or several base designs may be offered to the consumers, who can optionally personalize their bands by purchasing personalized/customized portions of the band (e.g., replacing all or portions of the band sizing assembly).

Figure 2:
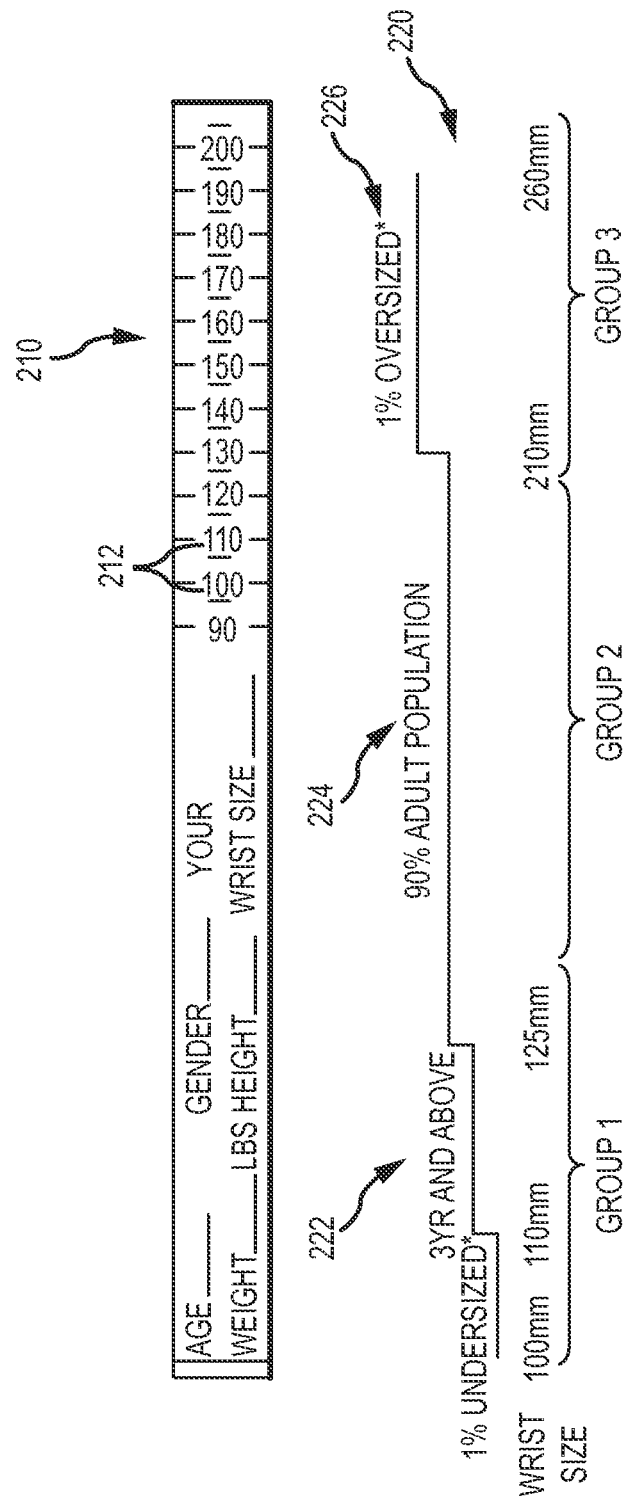
FIG. 2 illustrates a tape measure or tool that may be used by a purchaser/wearer of a band assembly to size their wrist and further illustrates a graph showing grouping of wrist sizes or ranges of wrist sizes to correspond to lengths/sizes of a band assembly (such as the assembly of FIG. 1) via inclusion or exclusion of a number of band layers or band sizing elements (or simply "band elements" or "extensions")
Figure 3:
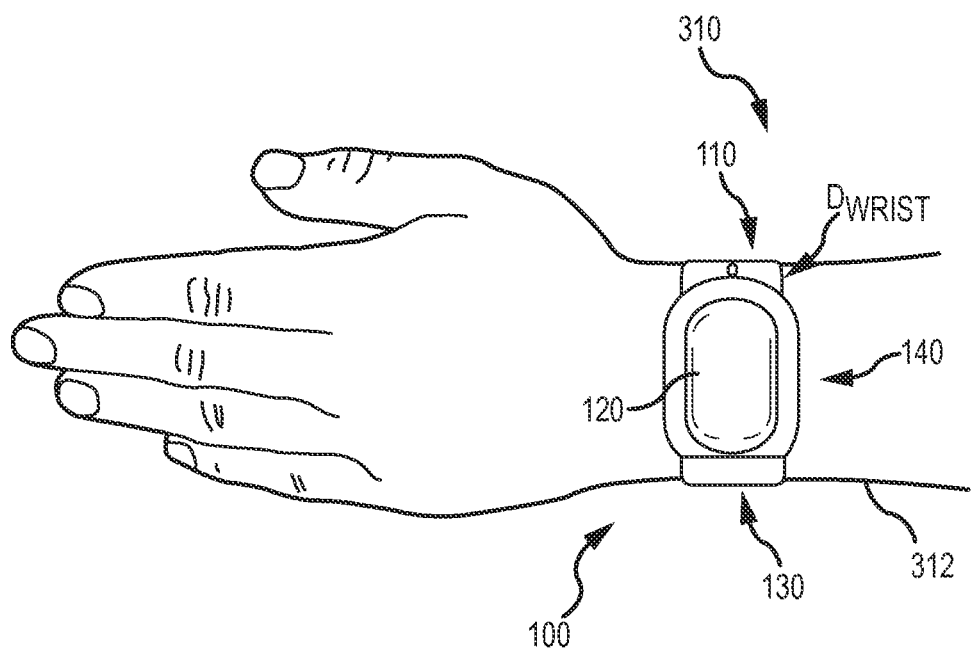
FIG. 3 illustrates a user or wearer wearing the band assembly shown in FIG. 1 with one (or more) of the band layers or band sizing/extension elements included so as to size the wrist assembly to the wrist of users/wearers (e.g., including more layers/elements increases the size of the band while peeling away or removing layers/elements reduces the size of the band)

In one example, an adjustable RFID wristband is provided that can be manufactured from a variety of modern day materials including plastics, rubbers, and silicones and even, in some cases, metals, leathers, cloths/textiles, and other materials. The wristband is fully adjustable by the wearer to suit their wrist size and also provides an aesthetic appearance. The wristband is also adapted to provide a secure wristband fastening mechanism that during regular wear can be fastened and unfastened by the wearer with exceptional ease (e.g., the band supports reuse rather than being a one-time product as was the case with many prior one-size-fits-all straps). This embodiment may be thought of as providing a band assembly made up of a two-piece band design including a base or identification band element (e.g., see FIG. 4) and a band sizing assembly made up of two, three, or more "wearable" layers/band elements (e.g., see FIGS. 5 and 6). Each layer or element in the sizing assembly may be retained or removed (peeled away) to allow the wristband to cover or be used with a defined wristband size range or wrist size range (see FIGS. 2 and 3 showing exemplary sizing groups and an assembled wristband worn on a user's wrist).

Figure 1:
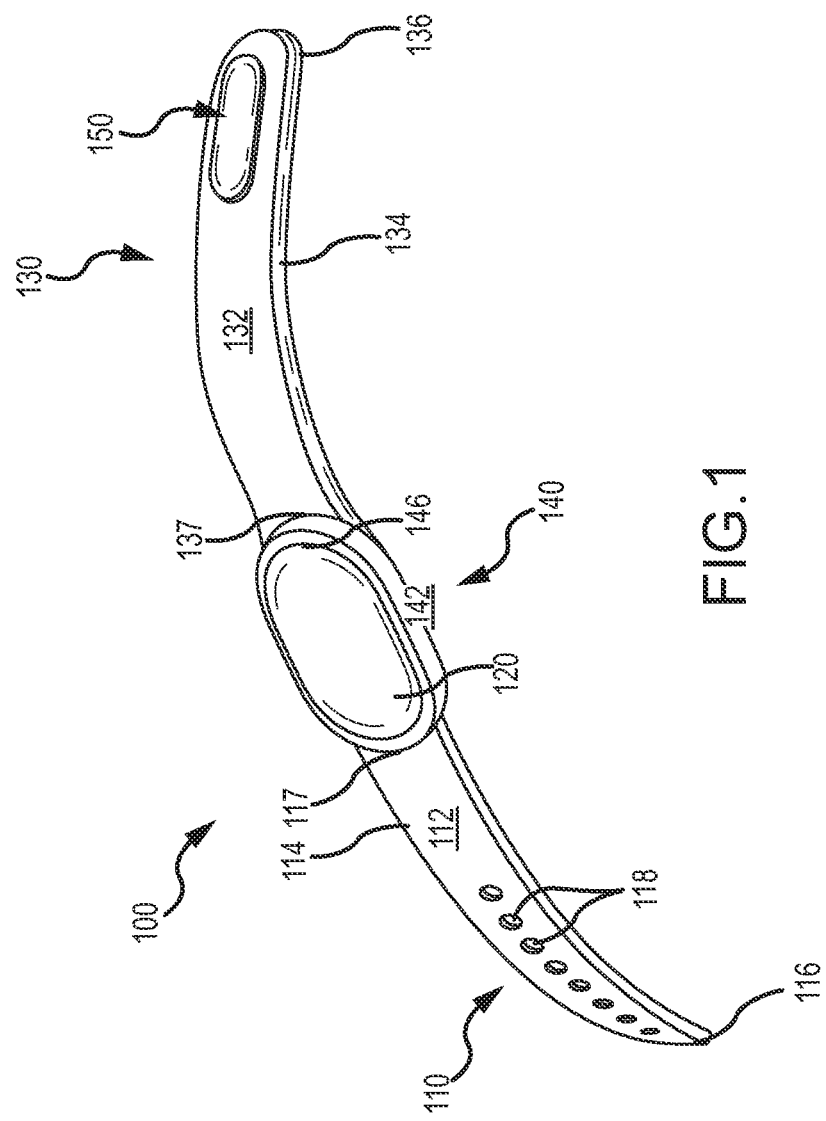
FIG. 1 is a top perspective view of a wearable band assembly of an embodiment of this description as may be delivered or provided to a purchaser or wearer (e.g., assembled to have a maximum or largest length such as to suit a maximum sized wrist or to suit a group or range of larger wrist sizes)
Figure 7:
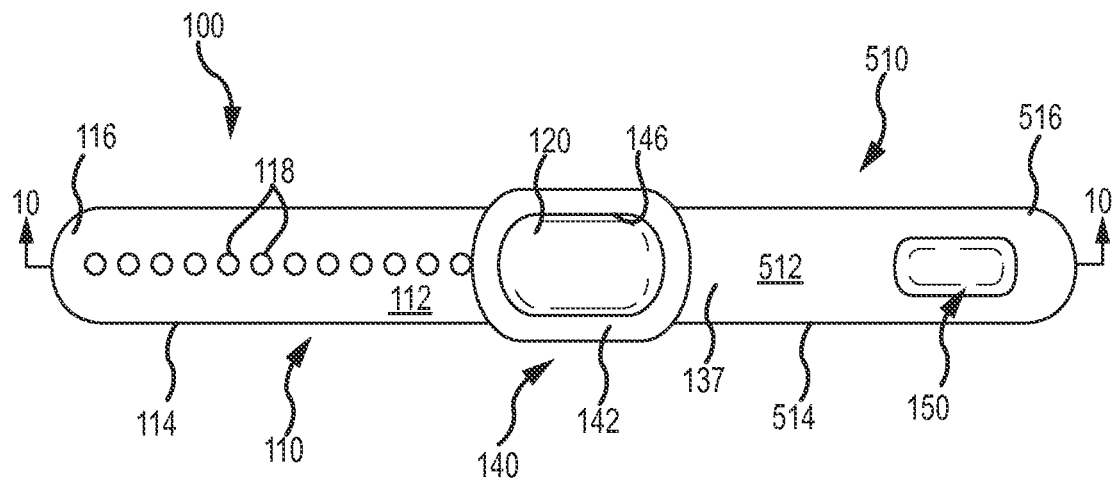
FIG. 7 illustrates a wearable band assembly formed by coupling the base band element of FIG. 4 with the inner layer or band element of the sizing assembly shown in FIG. 6 (e.g., to provide a band assembly suitable for a population with a relatively small wrist size)
Figure 8:
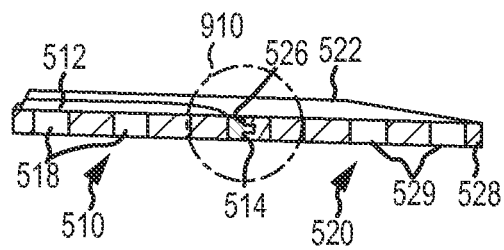
FIG. 8 illustrates a sectional view of the sizing assembly taken along line 8-8 and showing a coupling or interconnecting mechanism or assembly provided at the adjoining or mating edges/sidewalls of the band sizing layers/elements to facilitate tool-less connection and removal of the layers/elements to provide a multi-sizing mechanism with the band assembly.
Figure 9:
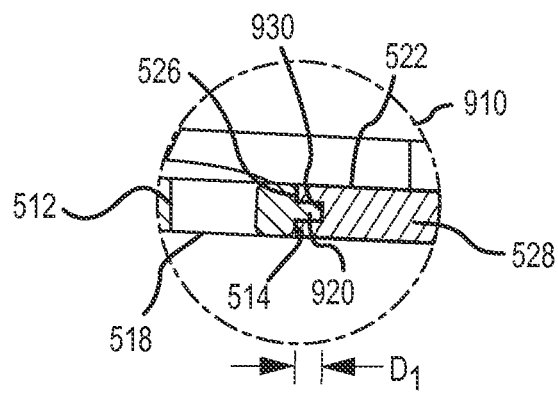
FIG. 9 is an enlarged view of the coupling or interconnecting mechanism shown in FIG. 8.

The inner band element of the sizing assembly includes a loop or lasso structure at one of its ends that may be coupled or mated with the identification portion or member provided on the end of the base band element (as shown in FIGS. 1 and 7 in assembled wristbands). Each of the band layers/elements of the band sizing assembly may have one or more edges/sidewalls that are designed to provide an interlocking/coupling mechanism that allows the layers/elements to be locked together and to be separated by the user to size the sizing band assembly and, consequently, the assembled wristband. For example, as shown in FIGS. 8 and 9, the interlocking/coupling mechanism may take the form of a peel away mechanism (e.g., a horizontally orientated tongue and groove arrangement similar to that found in some liquid beverage container caps with a removable security/sanitary band).

Figure 12:
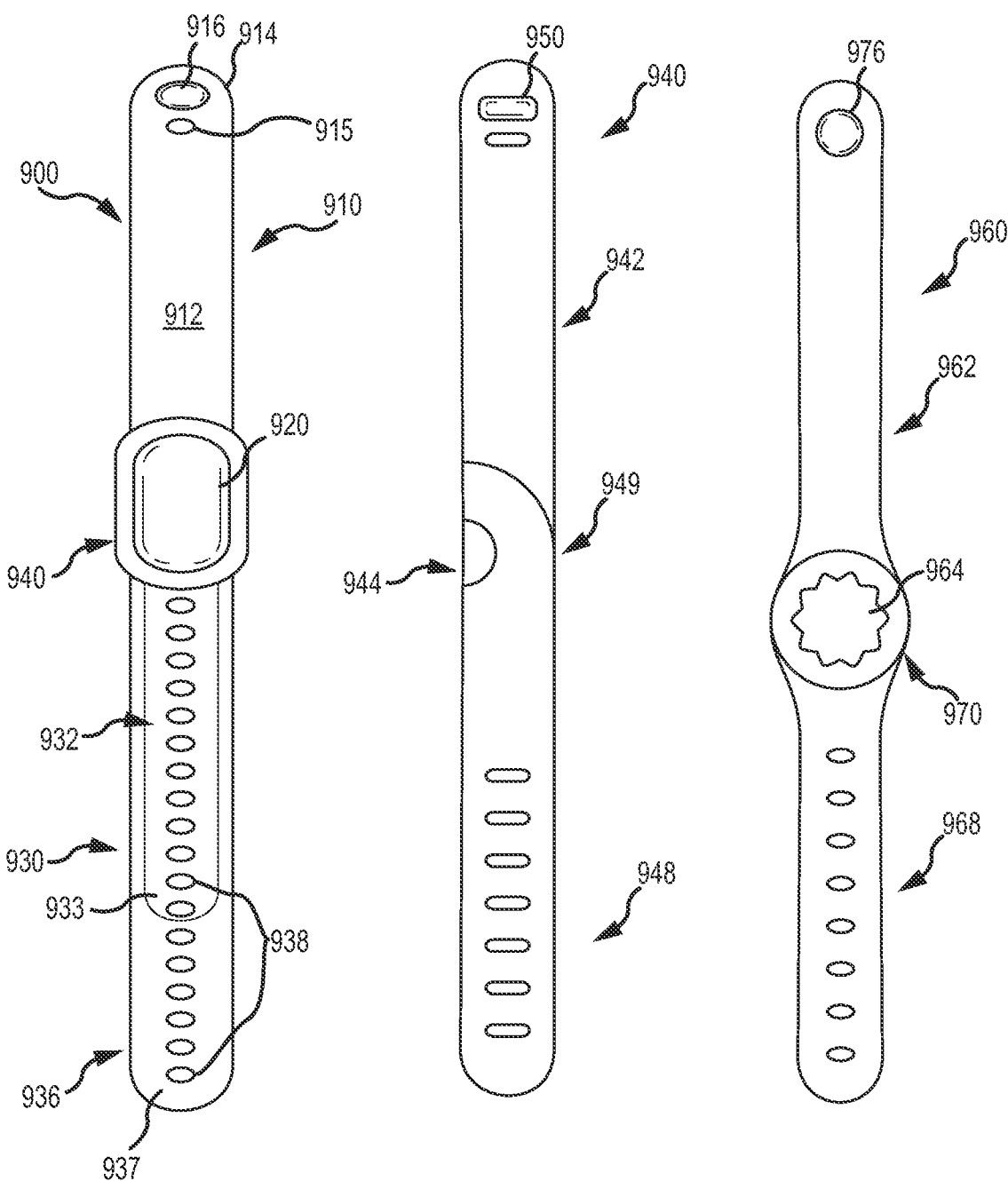
FIGS. 12A-12C show three embodiments of band assemblies that may utilize the interconnecting/coupling mechanisms of FIGS. 10 and 11 to provide a two-piece, wearable band assembly to provide two ranges of band sizes.

In use, the wristband assembly may initially be shipped or provided with all layers/elements assembled or coupled together such that the wristband is at its largest size or longest length (e.g., sized to fit a range of larger wrist sizes as shown in FIGS. 12A to 12C). The end users may then peel away layers or band elements from the band sizing assembly (e.g., an outer band element used to lengthen band sizing assembly when mated to the exterior or outer sidewall/edge of the inner band element in an assembly that is adapted to cover to wrist size ranges) to reveal or resize the wristband so that it fits their specific wrist size (e.g., wear "as is" or remove the outer layer or band element). In some cases, the removed layers may be replaced by other band elements, too, so as to allow the end user to personalize/customize their band as well as to size it to their wrists or to allow the wristband to be used on more than one wrist size (e.g., not permanently sized upon removal/peeling away a layer or band element).

Prior to the band designs presented herein, many wristbands used either an adhesive closure that is peeled away from the wristband or a separate, one-time plastic snap closure. The adhesive closures sometimes did not provide a desired closing strength and once removed could not be worn again. The plastic snaps provided a greater closing strength but were also often designed for one-time use, did not fit the wearer comfortably, and/or were too loose. With regard to other band applications, a typical wristwatch incorporates a buckle-style watch clasp. Similar to shoe manufacturing, most wristwatches are designed to a particular style with that same style or product run having a variety of wristwatch bands in different sizes to accommodate the specific end users' wrist sizes. However, similar to shoe shopping, when an end user purchases a wristwatch they try on different sizes of wristwatches (or wristwatch bands) of the same style to determine which band fits them appropriately. Because of the variability of different end user wrist sizes, the watch retailer must keep a large inventory of different wristband sizes to accommodate their customers, which significantly increases inventory costs for the retailer that may be acceptable in some settings (such as for higher end band products such as certain wristwatches).

However, in many fashion and wearer ID settings (such as entertainment venues and the like), it is much more desirable to be able to provide a one-size-fits-all solution or band design that can be sized by the seller or the wearer to suit their wrist size rather than carrying numerous versions/sizes of the band. The described wearable bands provide a "one size fits all" design that provides at least two and sometimes three or more wearable and user-selectable/interchangeable band sizing layers/elements in a band sizing assembly (e.g., the product or extension portion of the two-piece band design), with the inner band layer/element attached to the base band element via a loop or lasso provided at one end of the inner band layer/element. This configuration allows a venue operator or provider of bands to maintain one common base band (e.g., the intelligence or ID portion of the two-piece band) inventory and one or more sizing band elements that together accommodate a wide range of wrist sizes (e.g., address the multi-sizing problem associated with serving large audience/customer bases).

FIG. 1 illustrates one embodiment of a wearable band assembly 100 that may be used to provide a single band product that can be worn or used by people (i.e., wearers or users) with wrist sizes that fall within one of two, three, or more predefined size groups. The band assembly 100 may be thought of as providing a two-piece band design that includes a base band or base band element 110 and a band sizing assembly 130. The band assembly also includes a clasp 150 for fastening the interconnected or coupled band element 110 and sizing assembly 130 to a wearer's wrist (as shown in FIG. 3). The wearer may simply peel away or remove layers or sizing elements from sizing assembly 130 (and reposition the clasp 150 as appropriate in holes in body 132) to size the band assembly 100 to fit their wrist.

Figure 4:
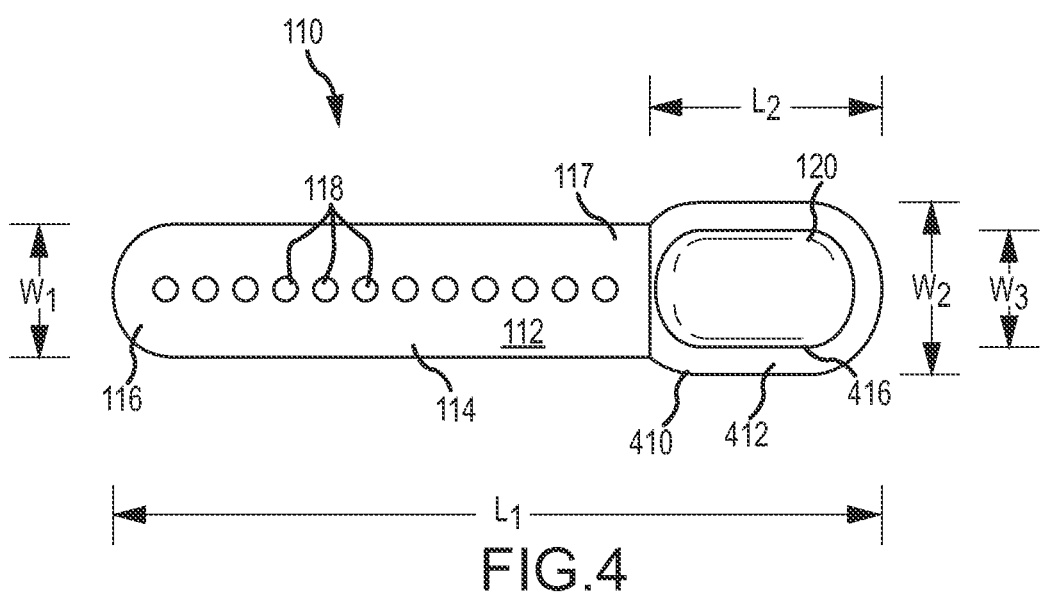
FIG. 4 illustrates the base or identification band element (e.g., band piece with an RFID module or the like)
Figure 10:
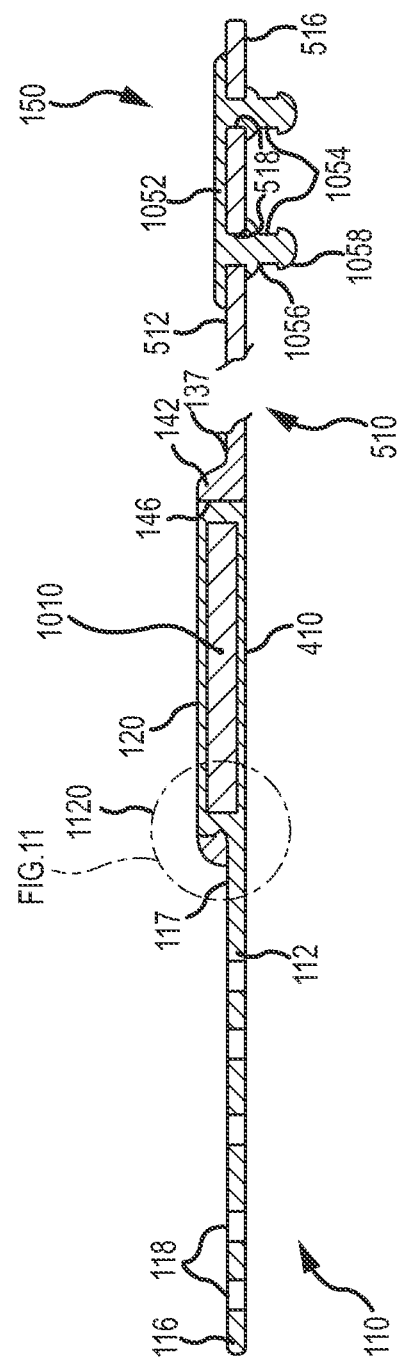
FIG. 10 is a sectional view of the band assembly of FIG. 7 taken along line 10-10 showing the coupling of the lasso portion of the inner sizing layer/band element to the identification/intelligence portion or member of the base band element.
Figure 11:
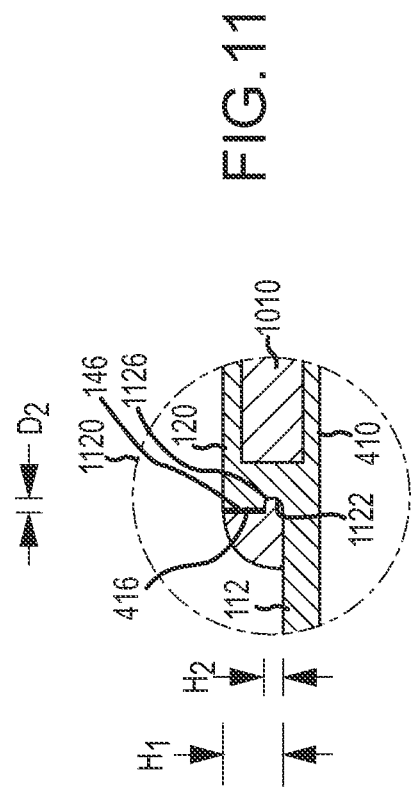
FIG. 11 is an enlarged view of the connection or joining provided within the band assembly of FIGS. 7 and 10.

The band element 110 may be thought of as the base or, in some cases, intelligence (or ID) band or component as this layer/element 110 is included in each configuration of the band assembly 100. The base band 110 has a body 112 that extends from a first end 116 to a second end 117 where it is connected to or where in includes a head (or, in many embodiments, a user identification member) 120. The shape of the body 112 is defined by an outer edge or sidewall 114 that extends about the periphery of the body 112, and, as shown, the body may be rectangular with a rounded or circular end 116 and head 120. The head/user identification member 120 of the body 112 also includes a portion of a coupling or interconnecting mechanism (such as shown in FIGS. 4, 10, and 11 or other configuration useful for connecting two bands 110, 130 of the assembly 100) used to connect or lock it to adjacent/overlapping sizing assembly 130.

The body 112 also include a number of holes 118 extending through its thickness at least at the end 116 such that the clasp 150 may be inserted into or mounted on a hole 118 in end 116 and then the clasp 150 may be extended through a hole in the opposite end 136 of the band assembly 100 (found in body 132 of sizing assembly 130) to securely close the band assembly 100 upon a wrist when the band assembly 100 is configured/sized (by selecting layers/elements of body 132). The base band 110 also may include an identification technology portion 120 connected at 117 to body 112 such as in embodiments in which the band assembly 100 is adapted for identifying the wearer such as by the inclusion of an RFID transceiver or RFID element embedded within the ID technology portion (or user identification member) 120 of the body 112.

The band assembly 100 also includes a second piece in the form of a band sizing assembly 130 that can be selectively coupled to the edge of the head or user identification member 120 as part of sizing or personalizing the band assembly 100. As shown, the band sizing assembly 130 includes a body 132 that extends from a first end 136 (which may have holes for receiving/mating with clasp 150) to a second end 137. As is explained below, the body 132 is formed of an inner layer or sizing element/extension about which one or more outer layers/sizing elements may be provided to provide a user adjustable or sized assembly 130 (and band assembly 100). The shape of the body 132 is defined in part by the outer sidewall or edge 134 that extends about the periphery of the assembly 130. The body 132 may be generally rectangular in its outer shape with rounded end 136 as defined by the outer edge or sidewall 134. Also, like the base band 110, the body 132 of the sizing assembly 130 may include a number of holes in or near end 136 such that the clasp 150 (with a clasp head or portion larger than the holes being shown in FIG. 1 that prevents it from passing through the holes) may be mounted on the sizing assembly 130 (or on body 112 of base band 110).

Significantly, the sizing assembly 130 includes a loop or lasso component 140 to allow the base band or base band element 110 to be mated with or captured by the sizing band assembly 130 (e.g., by inner sizing element of the assembly 130). The loop or lasso 140 is explained in more detail with reference to FIGS. 5, 6, 10, and 11 but, briefly, the loop or lasso 140 includes sidewall 142 that has an inner surface 146 that typically extends continuously (although this is not required) to define a hole for receiving the head 120, which protrudes or extends upward from the body 112 of the base band 110 (e.g., extends a height transverse to a plane containing the body 112 or the like). In some cases, the surface 146 of sidewall 142 is press fit onto the head 120 while in other cases (as shown in FIGS. 10 and 11) the loop wall 142 is snapped into place about the periphery of the head or user identification member 120 (e.g., with use of a raised rib or surface on the inner wall surface 146 that is received in a corresponding detent or recessed surface in the sidewall of the head 120 (or vice versa)). The hole defined by the inner edge/surface 146 generally has a shape and dimensions that match the dimensions and shape of the head 120 as defined by its outer edge/sidewall (e.g., the hole has a length and width that defines an oval or circular shape when the head 120 is oval or circular or the like).

The bodies 112, 132 may be formed of the same or differing materials, and these materials may vary to implement the assembly 100. In some embodiments, the bodies 112, 132 are formed of a plastic, a rubber (e.g., a silicone or the like), or similar material that may be relatively rigid but still be comfortable to wear and also be flexible to facilitate coupling of the two band pieces 110, 130 at the mating points between wall 142 and head 120 and coupling of the sizing layers or band elements of body 132. The number of holes 118 (and in body 132) may also be varied widely to practice the assembly 100 as well as the spacing between adjacent ones of the holes. Generally, one to three or more holes will be provided on each end 116, 136 such that the clasp 150 may be mounted and to allow connection of the two ends of a particular arrangement of assembly 130 and band 110 and to allow the band assembly 100 to be sized for a range of wrist sizes in each of its two or more configurations. In other words, the band element 110 provides a range of sizes with its holes 118 and the configuration of the band sizing assembly 130 with its sizing layers/elements (see, for example, FIG. 6) provides a range of sizes and the combination of band 110 with sizing assembly 130 provides a range of band sizes via the inclusion of the holes rather than a single size with each configuration.

FIG. 2 illustrates a tape measure 210 that may be used by a wearer to determine or measure their wrist size. The tape measure 210 includes markings 212 that indicate the measured size when the tape measure 210 is wrapped about the wrist and aligned with the end of the tape measure 210. As shown, in a human population, the smallest wrist size is typically about 90 millimeters (mm) while the largest wrist size is over 200 mm (such as about 260 mm or more). In one embodiment, the band assembly 100 may be provided or shipped with the tape measure 210, and the user/wearer may use the tape measure to determine their wrist size. This wrist size may then be used to determine whether to remove any of the interchangeable sizing layers/extensions in band sizing assembly 130 and if so, whether to remove one or more of the outer layers to properly size their wrist band assembly 100.

In this regard, graph 220 illustrates exemplary groups 222, 224, 226 that may be provided for a band assembly 100 for a typical human population. In this example, the band assembly 100 is a wristband and graph 220 represents differing wrist sizes for which it is desirable to provide a multi-sizing band assembly 100. As shown, a first group 222 that typically includes children and adults with a smaller wrists is shown (e.g., wrists of about 100 to 130 mm or the like). In the band assembly 100, the combination of the base band 110 and a first or inner sizing band element or layer of the sizing assembly 130 (e.g., the sizing extension with the loop 140) may be configured to provide an assembly 100 with a length covering this first group. Holes 118 may be used to allow the assembly 100 to be worn by people with wrists falling into the first group 222 (e.g., less than about 130 mm in "diameter").

A second group 224 may be defined or selected to include a range of "average" teens and adults. For example, the second group 224 may range from about 130 mm (or some number smaller to provide overlap with group 222 such as 125 mm) to about 190 mm or the like, and a second band sizing layer or element (or first outer layer or extension) may be included in the sizing assembly 130. In this manner, the combination of the base band 110 and sizing assembly 130 may have a length that is chosen in combination with the arrangement of holes 118 to allow the band assembly 100 with coupled bands 110, 130 to be worn by individuals having a wrist size between 130 and 190 mm (or other lower and upper bounds).

Finally, in this example, a third group 226 may be defined to include people with larger wrists such as wrists of 190 mm to 240 mm (or some other lower and upper bounds with the lower bound often being chosen to provide an overlap of the second and third groups 224, 226 such as 185 mm when the second group upper bound is 190 mm). A third band sizing layer or element may be provided in the sizing assembly 130 that is designed or chosen such that the assembly 100 now has a greater length such that this length when combined with the arrangement of holes 118 allows people with wrist sizes falling in the third group 226 to wear the band assembly 100.

In the following example, though, the band sizing assembly 130 is shown to only include two band sizing layers or elements (e.g., an inner layer/element and a selectively removable outer layer/element) such that the band assembly 100 may be worn by people with wrists of sizes falling into two groups instead of three (which may require more holes 118 to allow more adjustments via the connection with clasp 150). For example, the first group in such a two part assembly 130 may be to cover wrist sizes up to about 150 mm (or some other point within the adult population 224) while the second group would cover the rest of the population (or some predefined maximum size) such up to about 260 mm or the like.

FIG. 3 illustrates the use of the band assembly 100 in one configuration 310 to provide a band with a length sized to the particular wrist 312 and its diameter/size, $D_{wrist}$. In configuration 310, the band assembly 100 may be configured as shown in FIG. 1 to include all band sizing layers or band elements in body 132 of sizing assembly 130, and the sizing assembly 130 is coupled to the base band 110 via a lasso/loop 140 attached to user identification or head member 120. The two pieces 110, 130 are also coupled at their other ends 116, 136 via clasp 150 although this is not shown or is hidden from view in FIG. 3. The band assembly 100 may be sized to suit a first group of wrist sizes by retaining (or adding) one or more outer band sizing elements to the body 132 or to suit a second group of wrist sizes (a range of smaller wrist sizes) by removing/peeling away one or more band sizing elements from the body 132 (e.g., retaining just the inner sizing element with loop 140). In this manner in embodiments where the band assembly 100 provides user identification, the ID technology element 120 within base band element 110 is included in the band 100 in all configurations of the assembly 100 as is at least the inner sizing element of the sizing assembly 130 that provides the lasso/loop structure 140. In some embodiments, the sizing assembly 130 or one or more of its sizing elements may be exchanged or interchanged by the wearer for non-standard or original elements so as to customize the look to suit the wearer.

FIG. 4 illustrates in more detail the base band or base band element 110 that may be included as one piece of the two-piece band assembly 100 shown in FIGS. 1 and 3. The base band 110 has a body 112 that has a first length, $L_1$, that when combined with the length of the sizing band assembly 130 helps to define the overall length of the band assembly 100, and, in this regard, the length, $L_1$, may be about one half (or some other fractional amount) of overall length with the band assembly at it shortest or longest configuration (i.e., with only an inner sizing element or with one or more outer sizing elements or layers). The body 112 may be an elongated strip with an outer shape defined by the outer wall/edge 114 with a first width, $W_1$, extending from the outer or first end 116 to the inner or second end 117.

At the end 117, the body 112 includes (or is attached to) the head 120, which may be merely a fashion item or may include "intelligence" in the form of a timepiece, an identification module (such as an RFID module, a bar code, or the like), or other component that provides one or more functions for the user. In some embodiments, the head 120 includes an embedded RFID transceiver that is programmed for the intended wearer of the band 110. As shown, the head 120 is provided on a base or platform 410 of the body 112 that has a second width, $W_2$, that may be greater than the first width, $W_1$, of the body 112.

The platform 410 defines a shelf or shoulder 412 between the edge/sidewall of the platform 410 and the sidewall 416 of the head or user identification member 120 as the head 120 has a third width, $W_3$, that is less than the platform width, $W_2$ (e.g., about the width, $W_1$, of much of the body 112). In use as shown in FIG. 1, a loop or lasso 140 is slipped over the head 120 and abuts or is adjacent the sidewall 416 and is slid onto the head 120 until it abuts or is proximate to the shoulder surface 412. The lasso or loop 140 may simply capture the head 416 due to a press fit and friction between the bands 110, 130, but, often, a more secure coupling may be provided such as via a recessed surface at the lower portion of wall 416 near the shoulder 412 receiving a raised portion or rib on the inner surface 146 of sidewall 142 of the loop 140 (e.g., a snap detent arrangement).

Figure 5:
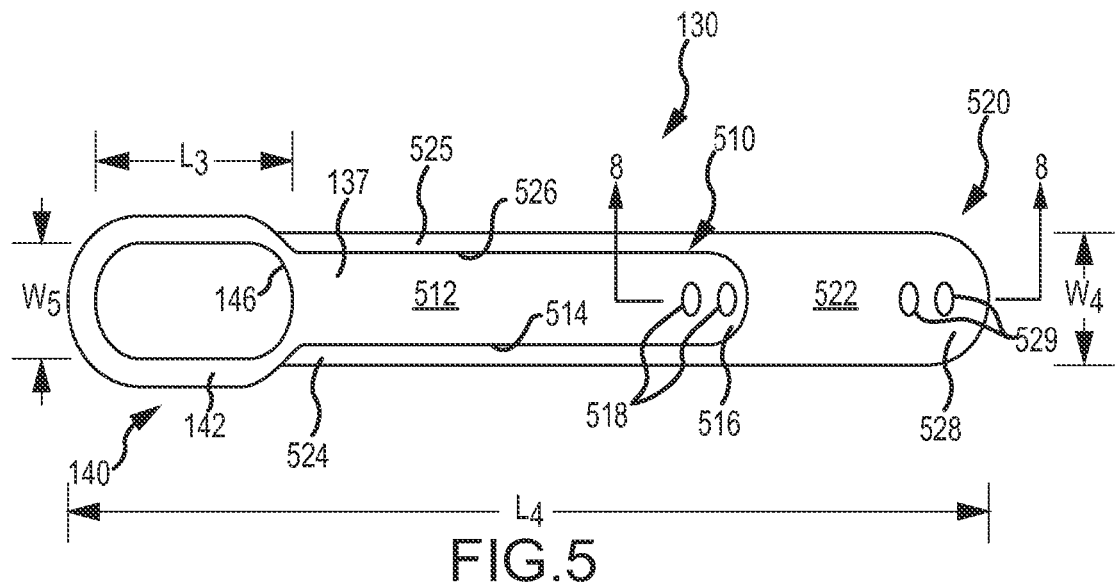
FIG. 5 illustrates the sizing or extension assembly with all sizing/extension band element or layers included such that the sizing assembly is at a maximum size (in this case, including two sizing elements but other embodiments may include 3 or more sizing layers)

To this end, FIG. 5 illustrates the band sizing assembly 130 that may be coupled with the base band element 110 to form a band assembly 100 sized to a user's wrist. As shown, the hole or receiving gap defined by the loop/lasso sidewall 142 and inner surface 146 has a length, $L_3$, that is about the same or some amount less than the length, $L_2$, of the head 120 to either provide a snug or even press fit (interference type fit) that is useful with many materials used for the head 120 and sidewall 142 such as a rubber or a plastic. Similarly, the hole or receiving gap for the head 120 may have a width, $W_5$, that is about the same as the head width, $W_3$, or somewhat less than such width to provide a snug capture or press fit of the loop 140 over the head 120 (e.g., friction between surface 146 and sidewall 416 of the head 120 resists installation and later removal of the loop 140 from the head 120).

The band sizing assembly 130, in this embodiment, includes an inner sizing layer or element 510 to which is coupled an outer sizing layer or element 520. FIG. 5 illustrates the outer sizing layer 520 coupled or interconnected to the inner sizing layer or element 520 to provide a sizing assembly 130 with a length, $L_4$, and this length, $L_4$, defines along with the length, $L_1$, of the base band 110, the overall length of a band assembly 100 that may be useful for wearing by people whose wrists fall within a range of larger wrist sizes. The inner sizing element 510 includes a body 512 extending from a first or outer end 516 (where clasp receiving holes 518 are provided) to a second or inner end 137 where the loop structure 140 is provided. The body 512 has a width and shape defined in part by sidewall or edge 514, and this sidewall 514 provides a portion of a coupling or interlocking mechanism when paired with inner sidewall or edge 526 of the outer sizing element 520.

Figure 6:
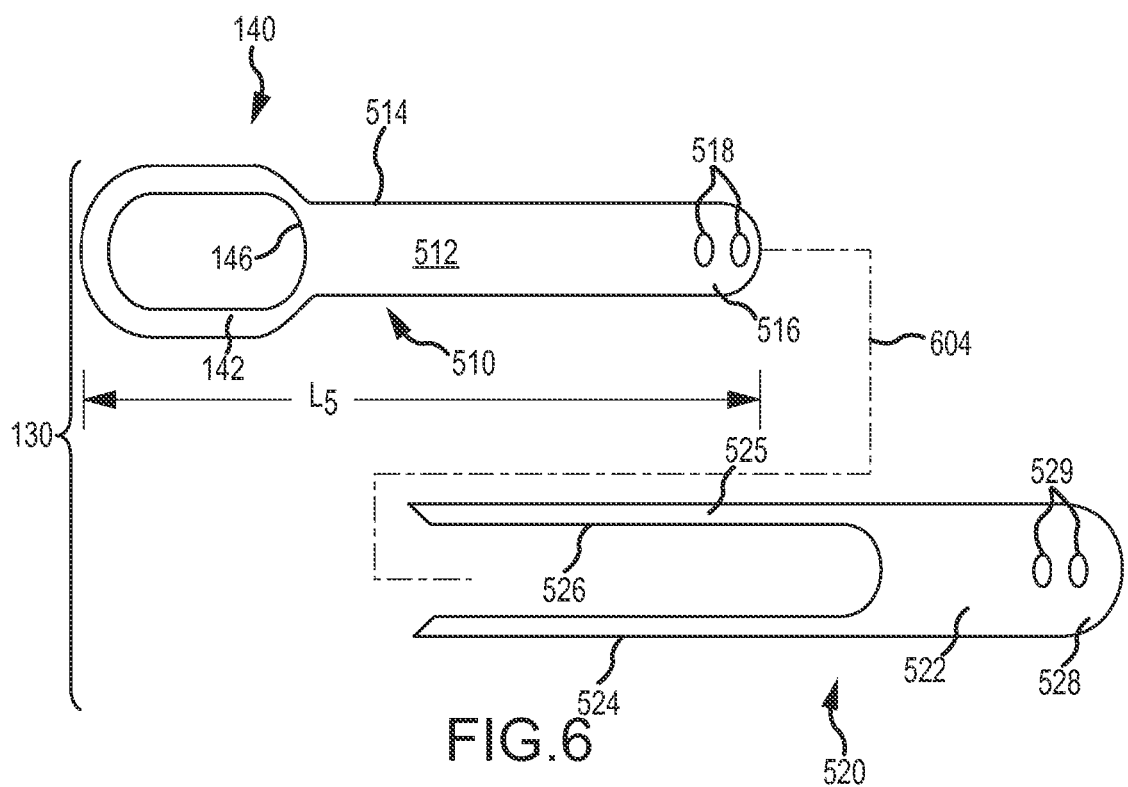
FIG. 6 is an exploded view of the sizing band assembly of FIG. 5 showing an outer layer or band element peeled away or separated from an inner layer or band element (which includes the coupling portion or lasso component for attaching to the base band element such as about the ID or intelligence portion/member)

FIG. 6 illustrates an exploded view of the band assembly 130 showing (with line 604) that the outer sizing element 520 may be selectively peeled away from and later reattached to the body 512 of inner sizing element 510. When the outer sizing element 520 is peeled away, the inner sizing element 510 has a length, $L_5$, which is shorter than the length, $L_4$, of the sizing assembly 130 shown in FIG. 5 and which may be desirable for defining a smaller size/length of the band assembly 100 as shown in FIG. 7, e.g., for wearers having a wrist size that falls into a group or range of smaller wrist sizes (e.g., less than about 150 mm, less than about 140 mm, or the like). The two-piece design of the assembly 130 allows a user to readily size the assembly 130 to suit their wrist size without requiring tools to remove and later reattach (in some embodiments) the outer sizing element 520.

The outer sizing element 520 includes a body 522 with spaced apart arms 524, 525 that extend away from the end 528 toward the loop 140. As shown, the arms 524, 525 are defined in part by an inner sidewall of the body 522, and this sidewall/edge 526 extends (when the two pieces 510, 520 are assembled) along the body 512 of the inner sizing element 510 so as to abut and couple/interconnect the body 522 of the outer sizing element to the body 512 of the inner sizing element. The sidewall 526 may define the inner surfaces of the arms 524, 525 as an elongated, narrow U-shape but such a shape, of course, will be varied to suit/receive the shape of the body 512 of the inner sizing element 510. The body 522 has a width, $W_4$, that is typically greater than the width of the inner sizing element body 512 but often less than the loop's outer surfaces. At the end 528, the body 522 may include one or more holes 529 extending through the body 522 to receive the posts/poppets of the clasp 150.

FIG. 8 illustrates a sectional view of a portion of the band sizing assembly 130 taken at line 8-8 in FIG. 5. As shown, the coupling or interconnection mechanism of the assembly 130 is provided via the configurations of the abutting or mating sidewalls 514 and 526 of the inner sizing element 510 and the outer sizing element 520. Specifically, these sidewalls 514, 526 may be mated along all or a portion of the periphery of body 512 as defined by sidewall or edge 514 of the inner sizing element 510 with the arms 524, 525 of the outer sizing element 520 layered onto or linked to the body 512. The coupling mechanism may take a number of forms to practice the assembly 100.

As shown in the enlarged view 910 of FIG. 9, an embodiment of the assembly or the band sizing assembly 130 calls for a tongue and groove arrangement to seal the two components 510, 520 where the sidewalls 514, 526 meet each other (e.g., periphery of body 512 or the like). As shown, the tongue and groove may be achieved by providing a post(s) 920 on the sidewall or edge 514, e.g., a centrally located post or rib extending outward a distance (e.g., equal to about the depth, $d_1$, of the recessed surface/groove 930). The post 920 may have a square or rectangular cross sectional shape as shown or take another shape, and the magnitude of the post height or recessed surface depth, $d_1$, may also vary to practice the assembly 100 (e.g., may be about one quarter to one half or more of the thickness of the body 512 or 522 (which may be about equal to each other)).

The outer sizing element 520 may provide the second half of the coupling mechanism with its sidewall 526 providing the groove or recessed surface 930 for receiving the post or rib 920. To this end, the surface 930 typically will have a depth, $d_1$, and cross sectional shape (such as width) corresponding to the post 920 (e.g., rectangular with same depth and width or somewhat smaller for a press fit or somewhat larger to ensure insertion of post 920). The walls of the post 920 and/or recessed surface/groove 930 may be textured to resist disengagement of the layers 510, 520 while a secure locking function may be furthered in some embodiments (not shown) by including a raised surface(s) or rib(s) on the sides of the post that fit into corresponding recessed surfaces or grooves in the sides of the recessed surface or groove 930.

Referring back to FIG. 7, a band assembly 100 is shown that may be created by the attachment of the inner sizing band 510 with the clasp 150 onto the base band element 110. Specifically, and as shown by FIGS. 5 and 6, the band sizing assembly 130 is modified by the decoupling or removal 604 of the outer sizing layer 520 from the inner sizing layer 510. This results in a shorter or smaller sizing band assembly 130 that only includes the inner sizing element 510 and has a length, $L_5$, which is shorter than the length, $L_4$, provided by the assembly 130 with inclusion of outer sizing element 520. As shown, the loop 140 is positioned with its sidewall 142 over the head such that the inner surface 146 of loop sidewall 142 is proximate to and, typically, captures the head 120 (or securely connects the two pieces 110, 510 together at a center portion of the band assembly 100).

FIG. 10 illustrates a sectional view of the band assembly 100 taken along line 10-10 in FIG. 7. The sectional view is useful for showing one configuration for the clasp 150. In this configuration, the clasp 150 includes a body or head 1052 that is larger than the holes 518 and, in this case, extends over two holes 518. The body 1052 may lie flush against or nearly flush against the body 512 of the inner sizing element 510 (or the body 522 of the outer sizing element 520 when the sizing assembly 130 is in an extended or expanded state to suit larger wrist sizes). The clasp 150 may include a pair of posts or poppets 1054 that extend out from the body 1052 a height or distance that typically exceeds at least about twice the thickness of the bodies 512, 522 and 112 such that band assembly 130 may be pierced by the posts 1054 as well as the thickness of the body 112 when the band assembly 100 is attached to a wrist.

The posts 1054 may include internal ribs 1056 to provide a shoulder of larger diameter (e.g., larger than the post and hole diameters) such that once the post 1054 is pushed through the body 512 it mates with the body 512 opposite the clasp body 1052 to resist the clasp 150 falling off (e.g., requiring force to be applied to remove the clasp 150 from the sizing element 510). Likewise, the posts 1054 may include ribs or heads 1058 at or near their ends with diameters exceeding the diameters of the holes 118 of the body 112 such that once the heads 1058 are pushed through the holes 118 the heads (or their shoulders) mate with the body 112 to resist disengagement of the base band element 110 from the sizing element (here inner sizing element 510 but in other cases element 520). The distance between a rib 1056 and a head 1058 on a post 1054 typically will match or slightly exceed the thickness of the body 112 and the spacing between posts 1054 typically will match the spacing between holes 118 in body 112 of the base band 110 and holes 518 in the sizing element 510 (or holes 529 in the body 522 of the outer sizing element 520).

More significantly, FIG. 10 shows one technique for providing the coupling mechanism for attaching the band sizing assembly (or sizing element 510 in this case) to the base band 110. As shown, at a second end 117 of the base band body 112, the user identification member 120 is provided and includes, in this example, an RFID module, tag, transceiver, or similar device 1010 on base 410. The RFID device 1010 may be over-molded with the plastic or other material of the body 112. As shown in enlarged view 1120 of FIG. 11, the ID member 120 may have a sidewall 416 that is generally vertical relative to the horizontal plane of the body 112 and base 410 such that the sidewall 416 extends outward at first height, $h_1$, adjacent the body 112 and, in some cases, about the rest of the periphery of ID member 120 as the base 410 may have a thickness equal to about that of the body 112 and also extend out from ID member 120 sidewall 416 to provide shoulder 412 for receiving the loop sidewall 142 (see FIG. 4).

As shown in FIGS. 10 and 11, the inner band sizing element 510 includes the loop or loop structure 140 at an end 137. The loop 140 is defined by a sidewall 142 that typically will have a height equal to about that of the ID member sidewall or $h_1$, and the sidewall 142 typically is shaped such that the inner hole or receiving opening matches the outer shape of the ID member 120 as may be defined by the sidewall 416. In this manner, when the two band pieces 110, 510 are mated together, the loop 140 extends about the periphery of the ID member 120 with the loop sidewall 142 contacting and capturing the ID member 120. Specifically, the "vertical" sidewall 146 may extend a distance equal to about the height, $h_1$, transverse to the plane of the body 512 of inner sizing element 510 and abut/contact the outer "vertical" sidewall 416 of the ID member 120, with the bottom or base of the sidewall 146 resting on or placed proximate to the receiving shoulder 412 of base 410.

To provide a snap fit and better retention of the loop 140 on ID member 120, the two sidewalls 146, 416 may be configured for providing a coupling fit such as a tongue and groove arrangement, a snap fit, or other interlocking design. A snap detent design is shown in FIGS. 10 and 11 with sidewall 416 of ID member 120 including a recessed surface or groove 1122 about the periphery of the ID member 120 proximate to the body 112 and base 410. The loop sidewall 142 includes a raised rib 1126 for mating with the recessed surface 1122 when the loop is pressed over the ID member 120 to have its base abut the shoulder 412 (e.g., the rib 1126 may be near the base of the loop sidewall 142), and the recessed surface or groove 1122 and the rib 1126 may be sized to match such as to have a height (or thickness), $h_2$, that is significantly less than the overall wall height, $h_1$, as well as a similar depth, $d_1$, to resist removal of the loop 140 from the ID member 120 (or disassembly of the two band pieces 110, 510 (or assembly 130)). The rib 1126 is shown to be semicircular in cross sectional shape but other shapes may be used (such as rectangular, triangular, or the like) and one rib 1126 is shown in FIGS. 10 and 11 but other embodiments may use 2 or more such ribs to provide the coupling mechanism of the band assembly 100.

FIGS. 12A to 12C illustrate several additional embodiments 900, 940, 960 of band assemblies 900, 940, 960 that may be used to implement a two-piece interlocking band design that allows a user to size a band, such as an RFID band, a watch, or the like, to their wrist. The band assembly 900 is similar to the assembly 100. The assembly 900 includes a base band 910 that may be combined with a band sizing assembly 930 via an interlocking or coupling mechanism provided via a central portion (e.g., ID member) 920 and a loop 940. The base band includes a body 912 with a first or outer end 914 with a series of holes 915, in which the clasp 916 is positioned, and with a second end to which the ID member 920 is attached (e.g., a raised or thicker portion of body 912 in which an RFID tag/chip may be provided). The ID member or center portion 920 is generally oval in shape in this example.

The band assembly 900 also includes a band sizing assembly 930 that is a two-piece construction made up of an inner band sizing element 932 and an outer band sizing element 936. The inner sizing element 932 has a body that extends from a first or outer end 933 to a loop 940, which may be an integral portion or separate part affixed or linked to the body. The loop 940 is designed with a sidewall defining an opening of size and shape to receive the ID member or center portion 920, and the loop 940 and member 920 have sides that provide a coupling mechanism (such as via snap detents as discussed above for assembly 100). The body of inner sizing element 932 includes numerous holes 938 arranged in a spaced apart but linear manner to allow a user to mate these with the clasp 916 to size the band assembly 900 when attached to a wearer's wrist. The band sizing assembly 930 also includes an outer band sizing element 936 with a body extending (with linearly arranged holes 938) from an outer end 937 about the periphery of the body of the inner sizing element 932 (e.g., with a tongue and groove or other interlocking arrangement) to allow the element 936 to be peeled away and then reattached. The body of the outer element 936 may have arms that extend the length of the body of the inner band sizing element 932 as shown or the attachment may be only along a portion of the periphery of the body of inner element 932.

As shown in FIG. 12B, the band assembly 940 differs from the assembly 900 in a number of ways. The assembly 940 is a two-piece assembly with a base band 942 with a clasp 950 provided in holes near one end of its body and a center portion or ID member 944 at a second, distal end. The second piece may be provided as a band sizing assembly 948 (with only the inner band sizing element shown in this figures as compared with FIG. 12A). The assembly 940 differs from assembly 900 in that the center portion 944 is not fully enclosed by the loop 949 of band sizing assembly 948. Instead, the center portion or ID member 944 is only captured or encircled for a fraction of its periphery such as about half of its sidewall. As shown, the ID member is a semi-circular shape as defined by its sidewall that extends up from the body of the base band 942 with a flat edge aligned with an outer edge/sidewall of the body of base band 942 and with a semi-circular or arched sidewall portion facing inward. The loop structure 949 in this case defines half a loop or lasso with its sidewall that is abutted against or placed in connecting contact with the sidewall of ID member 944 (e.g., with a tongue and groove or snap detent connection).

FIG. 12C illustrates another band assembly 960 similar to that shown in FIG. 12A with a full loop 970 encircling and coupling to a center portion or ID member 964. The band assembly 960 is again a two-piece design with a base band 962 with a clasp 976 attached to one end for attaching the assembly 960 to a wrist. The second piece is provided by the band sizing assembly 968, with only the inner band sizing element shown in this case with loop 970 at an inner or second end and holes extending along its length from an outer or first end to the inner end nearer the loop 970. The assembly 960 is useful for showing that the ID member sidewall and inner surface of the sidewall of the loop 970 may take a variety of shapes to provide a band assembly 960. As shown, the ID member 965 and loop 970 (or its opening or receiving gap) are generally circular with a textured surface (e.g., a star, a circle with ridges, or the like). Other cross sectional shapes for the ID member 964 will be readily apparent to those skilled in the art such as geometrical shapes such as triangles, rectangles, hexagons, and the like or more intricate patterns (e.g., outer shape of a character's head or body or the like).

The bodies of the band elements may generally have a single thickness, $t_{Band}$, such that the band assembly is a substantially planar and typically thin product or device (e.g., 0.0626 inches to about 0.25 inches may be a typical thickness range for a plastic or rubber band assembly). The ID component or central portion of the band assembly may be thicker than the other portions of the body and include a cavity or pocket that may hold an ID device (e.g., an RFID chip or transceiver) while in other cases the ID component may be replaced by a timepiece or a fashion/personalization component. The clasp may take many forms such as a multi-prong/poppet arrangement to engage two or more holes of one of the band elements.

The design of the described band assembly (e.g., assembly 100) provides one common band that can be provided to a large population of users. This minimizes the number of products that have to be manufactured and limits the inventory required to service the population. For example, one or two (or more) base designs (e.g., colors, lengths, shapes, and so on) of the band assembly may be produced for the base band and/or the band sizing assembly (or its components). Then, the end user can size the assembly to their wrist and also (optionally) customize the band assembly by replacing the base band or, more typically, the inner or outer sizing elements of the band sizing assembly with other elements (e.g., replace the inner or outer band sizing elements 510 or 520 with user-selected or user-specific components) that may have art or graphic treatments desired by the end user but that maintains the base/core band element 110 with its intelligence component 120 (such as the RFID technology that may be programmed for the buyer/consumer).

In some embodiments, the interconnection or coupling between the base band element and the band sizing assembly may be achieved with differing designs of the loop/lasso component and/or the user ID member. Also, it may be desirable to further enhance the personalization and/or customization of a wearable band assembly, and this may be achieved by providing an insert or cap that may be retained between the loop and the user ID member or head of the base band element.

Figure 13:
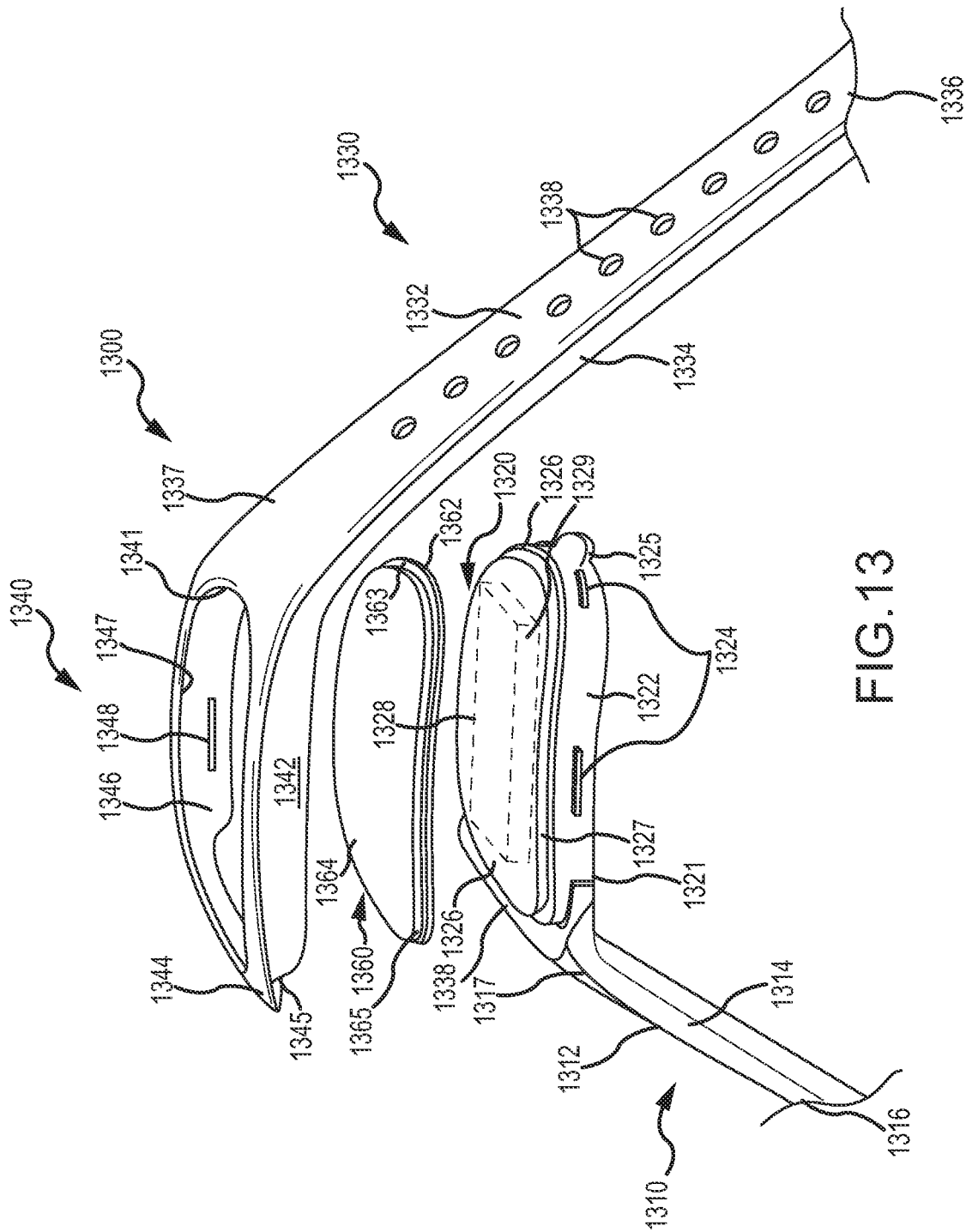
FIG. 13 illustrates an exploded or disassembled, partial view of another wearable band assembly that may include an optional decorative cap or insert that may be retained between a head/user ID member and a loop or lasso component.

FIG. 13 illustrates an exploded view of a wearable band assembly 1300 that generally includes a base band element 1310, a band sizing assembly 1330 with a loop/lasso 1340, and also an optional cap or insert 1360. The base band element 1310 has a body 1312 that has a shape defined by sidewall 1314 and extends a length from a first (or outer) end 1316 to a second (or inner) end 1317. At the first end, a clasp with prongs may be provided or posts/studs may be provided as integral components of the body 1312. Note, this is in contrast to prior embodiments in which the clasp was provided in the sizing band assembly with holes provided in the base band element body.

At the second end 1317, a user ID member or raised portion 1320 is provided in the base band element 1310. The user ID member 1320 may be configured with a base or platform 1321 defined to have a body enclosed by sidewall 1322, which extends about the periphery of the base 1321. To facilitate interconnection with the loop 1340, the user ID member 1320 may include two or more ridges or snaps (e.g., elongated, raised surfaces) 1324 extending outward from the sidewall 1322. These may take numerous forms and be of various numbers to practice the assembly 1300, but, as shown, the snaps 1324 may include two side snaps (one on each side of the base 1321) and two spaced apart snaps on the front or leading edge of the base 1321. To further assist in interlocking the user ID member 1320 with the loop 1340, a stop tab or tongue 1325 may also be provided on the leading edge of the base 1321 such as near the lower portion of the sidewall 1322, and the stop tab 1325 may extend outward more (e.g., two to four times) than the snaps 1324 and be longer and/or thicker than the snaps 1324 but this is not required. Additionally, to facilitate interconnection with loop 1340, a crease or recessed surface 1338 may be provided between the second end 1317 of the body 1312 and the sidewall 1322 of the base 1321 (e.g., a surface with a shape and size to receive a front wall/edge 1344 of the loop sidewall 1342).

The user ID member 1320 also includes a top surface 1326 with a shape defined by sidewall 1327 that extends upward from the base 1321, and the surface may be unadorned or adorned with a decorative element(s). To allow a cap 1360 to be received/retained, the sidewall 1327 is offset from sidewall 1322 a distance, which forms/provides receiving surface or ledge 1326 on base 1321. The body of the base 1321 may include an inner chamber 1328 in which a user ID element/device 1329 (such as an RFID module or the like) is positioned, as discussed in more detail above.

The insert or cap 1360 is configured to be fit over the top surface 1326 and rest upon ledge 1326. In some cases, the cap 1360 abuts sidewall 1327 such as when it is press fit or substantially friction fit onto the base 1321 of the user ID member 1320. The cap 1360 has a body 1364 on a base/platform 1362. The body 1364 may be hollow to receive the surface 1326 and defined in shape by sidewall 1365 that is offset a distance that creates surface/ledge 1363 (which may mate with a portion of the loop 1340 to retain the cap 1360 in the assembly 1300). The outer/upper surface of body 1364 may be decorated with one or more graphical elements or the like so as to allow the wearer to customize or personalize their particular implementation of the wearable band assembly 1300, and the caps 1360 are readily interchangeable such that they may be obtained separately and substituted to suit the wearer.

The sizing band assembly 1330 includes an elongated body or strap 1332 with a shape defined by sidewall 1334 extending from a first or outer end 1336 to a second or inner end 1337. The body 1332 may include a series of spaced-apart holes 1338 extending between these ends 1336, 1336 that may be mated with a clasp or posts/prongs provided on end 1316 of the base band element body 1312 to attach the assembly 1300 to a user's wrist or otherwise close the assembly 1300.

At the end 1337, the band sizing assembly 1300 includes a loop or lasso 1340 that is adapted both to interconnect with the user ID member 1320 and also to retain the cap/insert 1360 (when it is included in the assembly 1300). To this effect, the loop 1340 includes a sidewall 1342 that defines and extends about a periphery of an opening or hole 1341 through which the surface/top 1364 of cap 1360 may extend or be exposed (when flush or recessed relative to top of sidewall 1342). The sidewall 1342 is shown to terminate at ends or edges 1345, and the loop 1340 forms the hole 1341 in part with a leading or front sidewall 1344 that extends between the ends/edges 1345. The hole 1341 may be oval as shown or nearly any desired shape such as circular, square, triangular, or the like with the shape of the cap 1360 and surface 1326 being chosen to match the hole or opening 1341 (or vice versa).

The sidewall 1342 has an inner or mating surface 1346 that may abut or be proximate to the sidewall 1322 of the user ID member 1320 when the assembly 1300 is assembled. To receive and/or retain the cap 1360, the inner surface 1346 may include a lip 1347 extending completely or partially about the opening 1341, and the lip 1347 may mate with the ledge/surface 1326 on the user ID member 1320 and/or abut or be proximate to sidewall 1327. Additionally, interconnection is supported by the recessed surfaces (or simply recesses) 1348 provided in the sidewall inner surface 1346 for receiving the snaps/ridges 1324 along the side and front of the base 1321 (or in sidewall 1322).

FIG. 14 illustrates the wearable band assembly 1300 upon assembly. Specifically, the band 1300 has been formed by placing the cap 1360 over the surface 1326 of the user ID member or head 1320. Then, the leading or front edge 1344 of the loop 1340 was inserted or placed into the recessed surface or crevice 1338 between the body 1312 and head sidewall 1322 of user ID member 1320, and the loop 1340 was pivoted toward and over the user ID member 1320. The ridges or snaps 1324 snap or engage with the recessed surfaces 1348, and the stop tab 1325 abuts the body 1332 to resist further travel of the pivoting loop 1340. In this position, the cap 1360 is trapped between the loop 1340 and the user ID member 1320 with the cap 1360 resting on ledge 1326 and held down or in place at least by lip 1347. FIG. 14 also shows the band elements 1310, 1330 with their bodies 1312, 1332 coupled together via holes 1338 in body 1332 that receive and couple with posts or studs 1404 extending outward from an inner surface on the end 1316 of body 1312 of the base band element 1310 (and the studs 1404 may have larger heads that are received by recessed surface about holes 1338 in body 1332).

In some cases, the assembly 1300 may be formed without use or inclusion of the cap 1360. FIG. 15 illustrates such an implementation of wearable band assembly 1300. The loop 1340 extends about and interconnects (snap locks) with the sidewall of the user ID member 1320. As shown, without the cap 1360, the surface or top 1326 of the user ID member 1320 is visible and/or accessible via the hole or opening 1341. FIG. 15 is useful for showing that the cap 1360 is optional and that the loop 1340 is configured to couple with the user ID member 1320 with or without the cap 1360 being included in the assembly 1300.

FIG. 16 provides another exploded or disassembled view of the wearable band assembly 1300 providing additional component details. As shown, a recess 1649 is provided in the loop 1340 such as in lower portion of sidewall 1342 to provide a mating location or point for the stop tab 1325 when the loop 1340 is fully pressed (as shown with arrow 1608) over the user ID member 1320. FIG. 16 also provides additional details of the recesses 1348 in the inner surface 1346 of loop sidewall 1342 that are used to receive and provide a snap fit with front and side snaps 1324. The depth of the recesses 1348 may match or exceed the height of the snaps 1324 (e.g., up to 1 mm or more), and, as shown, the length of the front snaps 1324 may be some amount less than the side snaps 1324. Again, though, the number, size, spacing, and cross sectional shape of the snaps 1324 and corresponding recesses 1348 may be varied to practice the assembly 1300.

Figure 17:
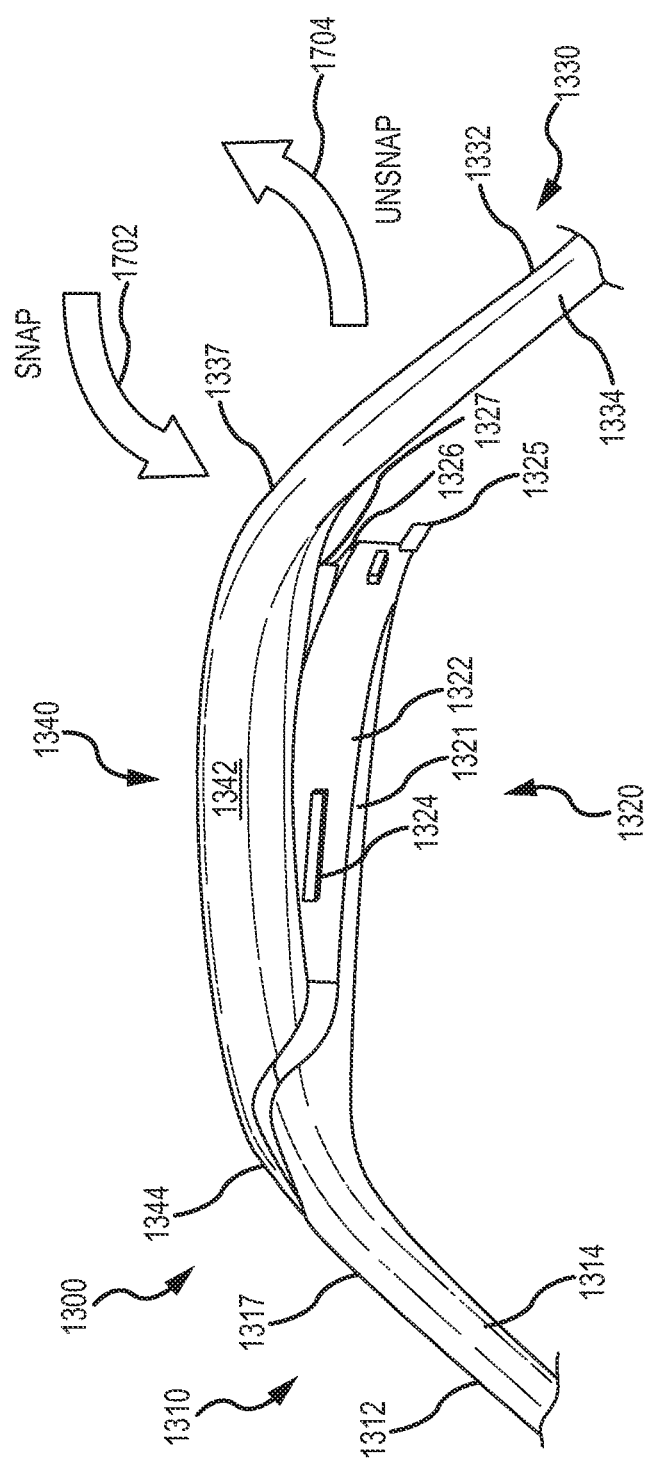
FIG. 17 illustrates the wearable band assembly of FIGS. 15 and 16 during assembly or disassembly by a user.

FIG. 17 illustrates how the wearable band assembly 1300 shown in FIG. 15 may be assembled 1702 or disassembled 1704 in a toolless and relatively easy manner by a wearer or user. As shown for assembly, the leading edge 1344 is fit against end 1317 (e.g., into valley 1338) and then the loop 1340 is pivoted 1702 to provide a snap fit or interconnection with the user ID member 1320. When assembled, the snaps or ridges 1324 are received into the sidewall 1342 in recesses 1348 and the stop tab 1325 fits into recess 1649. To later disassemble the band 1300 (such as to add an insert 1360 or change out band sizing assembly 1330 with a different assembly), the user simply applies a separating force to rotate 1704 the body 1332 away from the base band element 1310 which applies a force on pivot point provided by front/leading sidewall 1344 in recess 1338 such that the snaps 1324 are pulled out of the recesses 1348 in sidewall surface 1346 (unsnapped).

Figure 18:
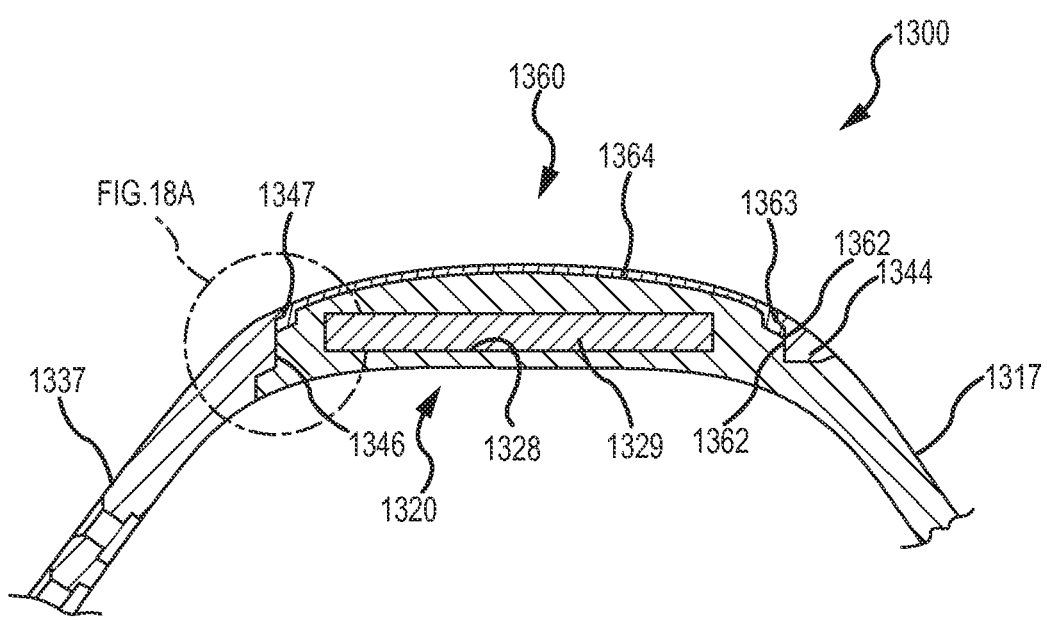
FIG. 18 illustrates a sectional view of the wearable band assembly of FIG. 14 showing interconnection of the lasso component with the base band element (or its user identification member) and retention of the cap or insert by the lasso component.
Figure 18A:
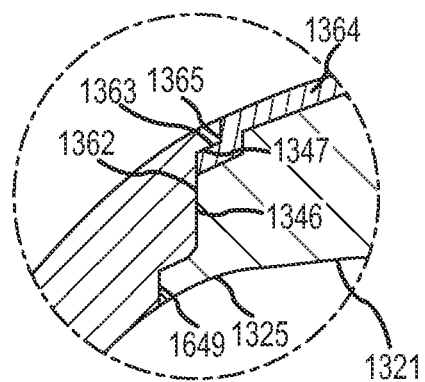
FIG. 18A illustrates an enlarged view of the lip shown in FIG. 18.

FIG. 18 provides a sectional view of the band assembly 1300 shown in FIG. 14 showing the interconnection of the user ID member 1320, cap 1360, and loop 1340. As shown, the cap 1360 is placed over the surface 1326 of the user ID member 1320. The loop 1340 is interconnected with the user ID member 1320 with sidewall inner surface 1346 abutting the sidewall 1322 of the base 1321, with the front sidewall 1344 received in surface 1338 (e.g., abutting or proximate to body end 1317), and with the stop tab 1325 in recess 1649. The cap 1360 is sandwiched between the loop 1340 and the user ID member 1320 such that when the loop 1340 is snapped on, the cap 1360 is held in place in the assembly 1300. Specifically, the base 1362 of the cap 1360 is placed on ledge 1326 of the user ID member 1320 and the loop sidewall 1342 holds the cap 1360 in place via contact between the cap base 1362 and sidewall surface 1346, between the lip 1347 and retention surface 1363, and between sidewall 1365 and top edge of sidewall 1342 (or edge of lip 1347).

As can be seen with the band assembly 1300, the use of a lasso or loop 1340 for interconnecting the two-pieces or band elements provides a large surface area 1364 that can be used as a wearer's personal billboard to express their particular tastes (e.g., to show a favorite character or the like). In some embodiments, the loop 1340 and user ID member 1320 are formed of differing materials or of the same/similar materials but using differing colors, finishes, and/or patterns so as to exaggerate or highlight the part lines to emphasize the interchangeability of the lasso concept in the assembly 1300. A variety of materials may be used for the components such as polyurethane which may be laminated for the band bodies, for the loop sidewalls, and for user ID member (or its body/sidewalls). In some cases, it is desirable that the cap be formed of a harder and/or more durable material such as polycarbonate or the like when the band elements are formed of a soft polyurethane or similar material. In some cases, the loop 1340 and/or technology band head or user ID member 1320, though, are formed of a more rigid material than the band bodies 1312, 1332, which may be formed of a more flexible and/or softer material.

The above described invention including the preferred embodiment and the best mode of the invention known to the inventor at the time of filing is given by illustrative examples only. It will be readily appreciated that many deviations may be made from the specific embodiments disclosed in the specification without departing from the spirit and scope of the invention.

We claim:

1. An identification band, comprising:
   a base band comprising a body and a user identification member provided in a portion of the base band body; and
   a band sizing assembly comprising an inner band sizing element and an outer band sizing element,
   wherein the inner band sizing element includes a first coupling mechanism fowled within an inner surface for directly coupling with the portion of the base band body via a second coupling mechanism provided on an outer surface of the base band body,
   wherein the outer band sizing element is detachably coupled to the inner band sizing element,
   wherein the user identification member comprises a module with sidewalls extending along the body of the base band to provide mating surfaces for the inner surface of the inner band sizing element, and
   wherein the inner band sizing element is coupled to the outer band sizing element via a connection mechanism provided on abutting portions of an outer sidewall of the inner band sizing element and of an inner sidewall of the outer band sizing element, whereby the outer band sizing element is detachable from the inner band sizing element to define a length of the band sizing assembly.

2. The band of claim 1, wherein the second coupling mechanism comprises a tongue extending outward from the outer surface of the base band body and the first coupling mechanism comprises a groove, adapted for receiving the tongue, provided on the inner surface of the inner band sizing element.

3. The band of claim 1, wherein an outer sidewall of the portion of the base band body includes a recessed groove and wherein the inner surface of the inner sizing element includes a raised rib, whereby the inner band sizing element is coupled to the base band body with the inner and outer sidewalls in abutting contact with the raised rib received in the recessed groove.

4. The band of claim 1, wherein the user identification member stores information corresponding to a wearer of the band.

5. The band of claim 4, wherein the user identification member comprises a radio frequency identification (RFID) tag.

6. The band of claim 1, wherein the user identification member comprises an RFID device.

7. The band of claim 1, wherein the the outer surface of the base band body includes a groove and the inner surface of the inner band sizing element includes a raised rib and wherein the inner band sizing element locks onto at least the user identification member of the base band when the raised rib is placed within the groove, whereby the band sizing assembly is coupled with the base band.

8. The band of claim 1, wherein the base band body, the inner band sizing element, and the outer band sizing element each comprises a number of holes extending therethrough.

9. The band of claim 8, wherein the band further comprises a clasp with a post, the holes being sized and shaped for receiving the post, whereby the clasp is mountable on the base band body, the inner band sizing element, or the outer band sizing element.

10. The band of claim 1, wherein the inner band sizing element comprises an elongated planar body.

11. The band of claim 10, wherein the first coupling mechanism is a loop defined by a sidewall extending transverse to a plane passing through the inner band sizing element body to defined an enclosed space for receiving and engaging the portion of the base band body containing the user identification member.

12. The band of claim 11, wherein the loop extends about the entire periphery of the raised portion of the based band body when the band sizing assembly is coupled to the base band via the loop and the raised portion.

13. A wearable band, comprising:
    a first band element with a body having a shape defined by an outer sidewall, the first band element comprising at one end a portion with sidewalls extending transverse to a plane passing through the body of the first band element;
    a second band element with a body, wherein the second band element body comprises a loop formed within one end, the loop being defined by an inner surface of a wall extending outward from the one end of the second band element body, wherein the first band element is detachably coupled to the second band element via a coupling mechanism mating the inner surface of the wall defining the loop directly with the sidewalls of the portion of the first band element body and wherein each of the bodies is elongated and comprises a number of linearly arranged and spaced apart holes on opposite ends of the bodies; and
    a clasp for mating with at least two of the holes to couple two differing portions of the bodies.

14. The wearable band of claim 13, further comprising an RFID device provided in the portion of the first band element body.

15. An identification band, comprising:
    a base band comprising a body with a user identification member provided in a portion of the base band body; and
    a band sizing assembly comprising a band sizing element including a first coupling mechanism formed within an inner surface for selectively and directly coupling with a second coupling mechanism provided on an outer surface of the base band proximate to the portion of the base band body with the user identification member,
    wherein the band sizing element comprises an elongated body, wherein the first coupling mechanism includes a loop defined by a sidewall extending transverse to a plane passing through the band sizing element body to defined an enclosed space for receiving and engaging the base band body containing the user identification member, and
    wherein the loop extends about the entire periphery of the base band body when the band sizing assembly is coupled to the base band via the loop and the base band body including the portion containing the user identification member.

16. The band of claim 15, wherein the second coupling mechanism comprises a tongue extending outward from an outer sidewall of the base band body and wherein the first coupling mechanism comprises a groove adapted for receiving the tongue.

17. The band of claim 15, wherein an outer sidewall of the portion of the base band body includes a recessed groove and wherein the inner surface of the sizing element includes a raised rib, whereby the band sizing element is coupled to the base band body with the outer sidewall and the inner surface of the sizing element in abutting contact with the raised rib received in the recessed groove.

* * * * *